United States Patent [19]

Eaton

[11] Patent Number: 4,910,999
[45] Date of Patent: Mar. 27, 1990

[54] METHOD AND APPARATUS FOR CONDUCTING FOULING TESTS

[75] Inventor: Paul E. Eaton, Cedar Hill, Mo.

[73] Assignee: Champion Chemicals, Inc., Houston, Tex.

[21] Appl. No.: 270,036

[22] Filed: Nov. 14, 1988

[51] Int. Cl.⁴ ............................................. G01N 17/00
[52] U.S. Cl. ..................................................... 73/61.2
[58] Field of Search ....................... 73/61.2, 86; 374/7; 204/404; 422/53; 366/251, 249, 247, 245

[56] References Cited

U.S. PATENT DOCUMENTS

| | | | |
|---|---|---|---|
| 2,752,228 | 6/1956 | Gould | 73/86 |
| 2,931,219 | 4/1960 | Moorman et al. | 73/61.2 |
| 3,148,534 | 9/1964 | Benson | 73/61.2 |
| 3,166,932 | 1/1965 | Ellison | 73/86 |
| 4,098,662 | 7/1978 | Schell et al. | 374/7 |
| 4,383,438 | 5/1983 | Eaton | 374/7 |
| 4,422,771 | 12/1983 | Earhart et al. | 366/251 |
| 4,497,580 | 2/1985 | Doyel | 366/251 |
| 4,521,864 | 6/1985 | Characklis | 73/61.2 |

Primary Examiner—Robert R. Raevis
Attorney, Agent, or Firm—Gunn, Lee & Miller

[57] ABSTRACT

This invention relates to a laboratory device which produces a fouling deposit, under controlled temperature and pressure, which reproduces actual plant conditions, and accurately measures the deposit of foulant accumulated during the deposition process. The device is utilized for testing the fouling tendencies of a wide variety of fluids which change on contact with a hotter surface, forming a solid or semisolid deposits which stick to the surface. The apparatus has the capability of calibration and measurement of the probe temperature and temperature measurement changes with fouling, and may be advantageously related to the amount of fouling present. The apparatus includes multiple probes each removably supporting test wires which are electrically heated to selected temperatures for simultaneous multiple fouling tests by a constant heat flux or to a constant temperature.

15 Claims, 6 Drawing Sheets

METHOD AND APPARATUS FOR CONDUCTING FOULING TESTS

FIELD OF THE INVENTION

This invention relates generally to apparatus and procedures for carrying out fouling tests in a laboratory environment. More particularly, the invention relates to a fouling test procedure that is specifically designed to simulate any equipment that exposes a hot metal surface to a fluid containing a foulant. The test procedure is also designed to simulate a heat exchanger tube exposed to a fouling liquid medium and for determination and evaluation of the effect of physical parameters which affect the fouling rate of a process involving the specific parameters for which the test is conducted.

BACKGROUND OF THE INVENTION

The object of any laboratory test is to simulate some physical phenomenon as closely as possible, making sure that all of the physical independent variables are represented and controlled. Also the dependent variables must be measurable in a statistically meaningful manner. In the case of fouling tests, the independent variables of interest are fluid pressure, fluid temperature, surface temperature, fluid velocity, and fluid composition. The dependent variable is the actual mass or volume of deposit which accumulates on a particular surface in a given time. The dependent variable is referred to as the deposition rate. Another object of a laboratory fouling test is to determine an effect of an independent variable on the deposition rate. For example, the fluid composition may be changed by adding a variety of chemicals which may in turn affect the fouling rate.

One such as the inventor hereof, having spent many years in the field of fouling research and conducted many fouling tests, will have experienced frustration with the fouling tests because the fouling rate is difficult to control and is not very reproducible even when all other independent variables are controlled and/or held constant. Many of those experienced in this particular field claim to have fouling tests which have reproducibilities better than 10%. However, it has generally been conceded by those experienced in this art that fouling tests usually reproduce the fouling rate by no more than 50%. In many cases this makes the test useless in determining the effect of some independent variable, such as fluid composition, because the fouling rate changes more by itself than by changing the independent variable. Therefore, many tests must be conducted at the same conditions in order to produce statistically meaningful results. This can be costly and time consuming because each fouling test requires between 3 and 24 hours to complete.

The primary cause of the fouling of surfaces used to heat processed fluids is that dissolved or suspended contaminants which occur in the fluids are degraded when exposed at elevated surface temperatures, forming solids or semisolids in the form of polymers, coke, salts, and other inorganics. Therefore, it is critical that surface temperature be well known and controlled. The difficulties with controlling surface temperature is that there are so many other variables, than fouling deposits, which have a major influence. Some of the other variables are, fluid velocity, fluid composition, fluid temperature and system pressure. Only when all of these variables are controlled can meaningful laboratory fouling test data be gathered.

In designing apparatus and procedures of the type involved, the problem is to generate and measure in a laboratory environment a fouling deposit representative of that produced in the field. The information obtained by carrying out such fouling tests enables many antifoulant treatments to be evaluate as well as other factors which may mediate the fouling process.

My prior U.S. Pat. No. 4,383,438 describes fouling test equipment which is an example of fouling test apparatus for conducting single fouling tests for each cycle of operation, thereby requiring significant expenditures for conducting multiple tests. It is desirable therefore to provide fouling test apparatus having the capability of simultaneously conducting multiple tests to thus provide a wide range of useful commercially efficient test information within a reasonably short period of time.

During the conduct of fouling tests a quantity of the foulant leaves solution and becomes deposited on a heated foulant receptacle surface. The concentration of the foulant in the test solution is thus depleted by the quantity deposited and the rate of fouling can change. Subsequent fouling tests using this test fluid or another quantity of fluid from the same batch may not have satisfactory reproducibility. It is desirable therefore to provide a fouling test system wherein multiple fouling tests may be conducted through employment of a single test fluid sample and the results of the tests will exhibit optimum reproducibility.

It is a principal object of this invention to produce fouling tests for evaluating the effect of physical parameters which affect the fouling rate.

It is another feature of this invention to provide novel equipment that is capable of reducing the time and costs required to generate statistically meaningful fouling test data.

It is a further feature of this invention to provide means for simultaneously conducting a plurality of fouling tests during each test procedure.

It is also another feature of this invention to provide means for insuring that independent variables such as fluid velocity, fluid temperature, surface temperature and fluid composition are well known and controlled.

It is an even further feature of this invention to insure that the laboratory fouling data of this invention is comparable to data collected from actual plant environments.

It is another feature of this invention to provide means for efficiently calibrating the fouling probes of the apparatus so that surface temperature is well known.

SUMMARY OF THE INVENTION

Fouling test apparatus representing a preferred embodiment of this invention comprises a pressure vessel having means for controlling the temperature of test fluid contained within the vessel and having means for maintaining predetermined pressure within the vessel during respective test procedures. A plurality of fouling probes are supported by the pressure vessel, preferably by the upper portion thereof, and extend into the fluid under test. Each of the fouling probes is sealed within the pressure vessel and incorporates a replaceable fouling test wire which is electrically heated to induce deposit of fouling composition thereon. Each of the probes incorporates inner and outer conductor elements with an electrical insulator positioned therebetween and arranged so that the fouling test wire has its ends coupled respectively with the inner and outer conductors. Each of the probes also incorporates a constant temperature or constant power supply and a voltmeter to determine the resistance of the fouling test wire. During a fouling test procedure the probes may be operated at differing temperatures designed for each of the multiple tests being conducted.

The pressure vessel defines an annular chamber containing the test fluid. A stirring means is provided for the high pressure test chamber and may be in the form of a rotating cylinder supported by bearings within the chamber and rotated by means of an externally mounted variable speed drive motor having a drive shaft extending through a sealing gland into the pressure vessel. As the rotating cylinder is rotated by the variable speed drive motor, such motion induces rotary movement of the fluid within the annular test chamber, thus causing the fluid to flow at a constant flow rate past each of the fouling probes or simulation of fluid flow conditions past each test probe.

The fouling test system is provided with a computer that receives various signals according to the operating parameters of the apparatus. For example, pressure signals identifying internal chamber pressure, tachometer signals identifying the velocity of cylinder rotation and controllable constant heat flux signals of the power supply for the fouling probes are conducted to the computer, processed and appropriately displayed. The computer also receives, processes and displays signals identifying the constant temperature power supply for the external heating mantle of the test chamber.

A test sample of the fluid to be tested is placed into the fouling test pressure vessel. A closure provided with a plurality of fouling probes is then fixed in sealed relation to the pressure vessel. Each of the fouling test probes includes a replaceable electrically heated wire to obtain a fouling sample. The body of fluid under test is then brought to, and maintained at, a substantially constant elevated temperature. The fouling test procedure also includes heating the wires of the probes to their respective temperatures by supplying an electrically energized heat input into the wires.

As the wires of the probes are heated the stirrer is energized and caused to rotate by its variable speed electric motor, thus imparting rotation to the rotatable stirring cylinder. The stirring cylinder induces rotation of the fluid within the annular chamber of the pressure vessel thus simulating the flow of fluid past the probes. After the fouling test has been completed, the closure is removed from the pressure vessel and the test wires of the robes are removed, weighed and compared to the weight thereof prior to the fouling test procedure to provide an indication of the foulant contained within the sample.

Each of the probes is calibrated by means of a thermocouple and an oil heater prior to each fouling test by recording probe resistance vs. oil temperature during the heat up cycle of each test run. The current is then increased in order to achieve desired wire temperature. Two modes of continuing the test are used: (1) for constant temperature operation current is first applied to get a starting temperature, then the controller is set to maintain this temperature throughout the test. As fouling deposits accumulate the current required to maintain constant temperature declines. The current vs. time is used to generate a "current fouling curve" which is subsequently converted to a fouling curve using a fouling equation as set forth hereinbelow and is used as an insitu fouling monitor. (2) For constant heat flux operation, a heat flux is applied sufficient to bring probe to the desired temperature. This heat flux is maintained constant throughout the remainder of the test, during which time the probe surface temperature rises as a result of the insulating properties of the deposit. The theory shows that the temperature increase is directly proportional to the deposit amount and again can be related to a fouling fact or using the fouling equation.

Similar tests are conducted with a quantity of anti-foulant present within the fluid under test. If the test wires of the probes exhibit zero or negligible fouling, the presence of anti-foulant within the fluid from which sample was taken will eliminate or minimize fouling of equipment during actual operating conditions.

BRIEF DESCRIPTION OF THE DRAWINGS

So that the manner in which the above recited features, advantages and objects of the present invention are attained and can be understood in detail, a more particular description of the invention, briefly summarized above, may be had by reference to the embodiments thereof which are illustrated in the appended drawings.

It is to be noted, however, that the appended drawings illustrate only typical embodiments of this invention and are therefore not to be considered limiting of its scope, for the invention may admit to other equally effective embodiments.

DETAILED DESCRIPTION OF PREFERRED EMBODIMENT

Figure 1:
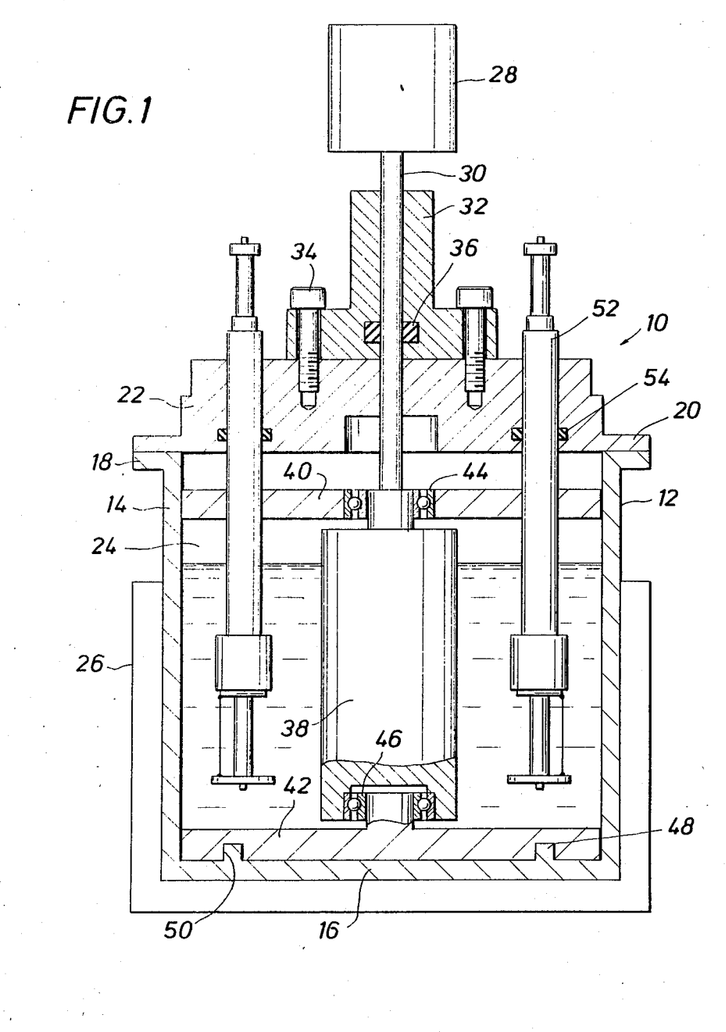
FIG. 1 is a partially mechanical and partially schematic illustration of a preferred embodiment of the fouling test apparatus and system of this invention.

Referring now to the drawings and first to FIG. 1, a pressure vessel is shown generally at 10 comprising a lower vessel structure 12 having a sidewall 14 and a bottom wall 16. The upper portion of the pressure vessel is provided with a flange member 18 providing a seat for a corresponding flange 20 of a vessel closure member 22. The closure 22 is secured to the vessel 12 such as by clamping or by any other suitable means of connection to insure the maintenance of a predetermined pressure within the test chamber 24 of the vessel. The vessel 12 is provided with externally applied heating by means of an outer heating jacket or mantel 26 which is disposed about the side and bottom walls of the pressure vessel. The heating mantle is heated electrically by a source of constant current as described hereinbelow in connection with FIG. 3. A variable speed electric motor 28 is axially positioned relative to the test chamber 24 and includes a rotary shaft 30 that extends through a sealing and support gland 32 secured by bolts 34 to the closure member 22. A seal member 36 of any suitable type is disposed within the sealing and supporting gland and provides a high pressure fluidized sea between the motor shaft SO and the gland 32.

A rotating cylinder 38 is supported within the test chamber 24 by upper and lower support elements 40 and 42 having upper and lower bearings 44 and 46 providing rotatable axial support for the cylinder 38 within the test chamber. The lower support 42 establishes mechanical interlocking with respect to the lower wall 16 of the cylinder. This is accomplished by projections 48 which extend from the lower wall 16 and which are received by respective grooves or slots 50 formed within the lower support element 42. The drive shaft 30 of the motor 28 is secured in driving relation with the cylinder 38 for rotation of the cylinder to develop fluid circulation within the test chamber 24 that simulates a condition of fluid flow.

A plurality of fouling probes 52 are supported in sealed relation by the closure 22 with lower portions thereof being positioned substantially mid way between the vessel wall and the wall of the rotating cylinder. The fouling probes 52 are sealed with respect to the closure by means of a plurality of sealing elements 54 having the capability of withstanding chamber pressure. Each of the probes 52 extends through respective openings in the support element 40 and functions to stabilize the support element within the test chamber.

Figures 2, 4:
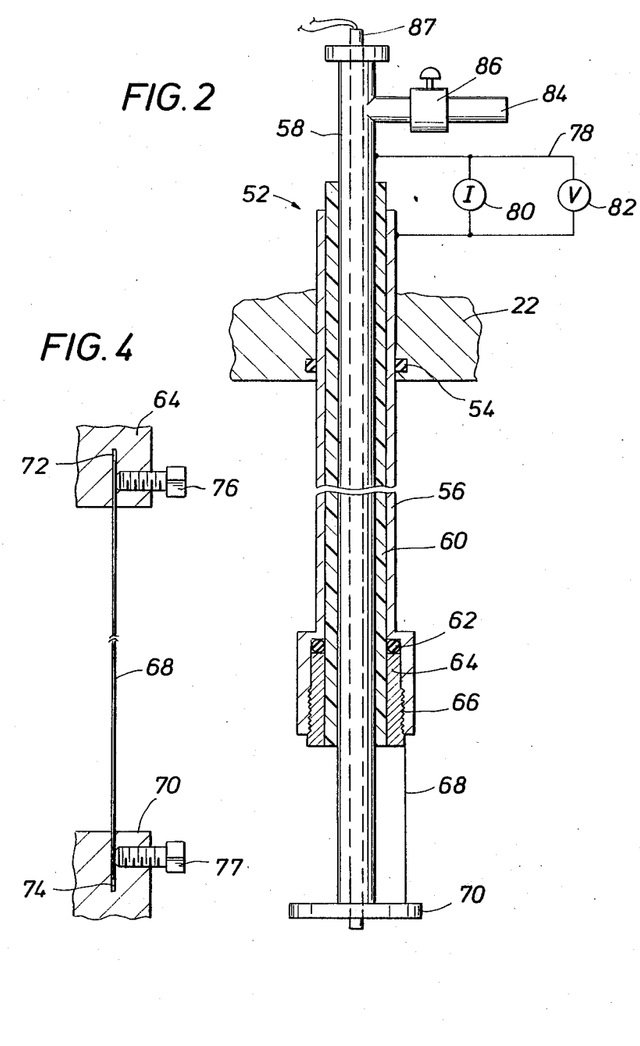
FIG. 2 is a vertical section illustrating one of the fouling probes of the apparatus of FIG. 1.
FIG. 4 is a fragmentary sectional view of the probe apparatus of FIG. 2 illustrating removable attachment of fouling test wires to the of FIG. 2.

Each of the probe elements may conveniently take the form shown generally in the form at FIG. 2 wherein an outer conductor tube 56 extends through the closure 22 and is sealed with respect to the closure by means of a suitable sealing element 54. An inner conductor 58 extends through the tubular outer conductor and is separated from the outer conductor by means of a tubular electrical insulator element 60. The insulator 60 is sealed with respect to the outer conductor 56 by means of a circular sealing element 62 which may take the form of an O-ring or any other suitable seal. The sealing element 62 is secured by means of a seal retainer 64 which is threadedly secured to an enlarged lower portion of the outer conductor by means of a threaded connection 66.

A fouling test wire 68 is secured by the probe structure and is in electrical contact with the inner conductor at its lower end by means of a test wire support flange 70. The upper end of the test wire is maintained in contact with the outer conductor 56 by means of a connection with the O-ring retainer 64 or the enlarged outer portion of the outer conductor. As shown in FIG. 4, the test wire 68 may be removably supported in assembly with the probe structure with its upper and lower ends positioned respectively within upper and lower receptacles 72 and 74 and with screws 76 and 77 or other suitable restraining devices removably securing the test wire in place. As shown schematically at the upper portion of FIG. 2, the test wires are each provided with a heating circuit 78 which is a schematic simplification of a part of the Controller/Monitor circuitry. The heating circuit 78 is provided with a source of electrical energy 80 which is provided by the power supply of the Controller/Monitor. Heating the test wire is accomplished by the circuit 78 with the temperature of the test wire being controlled by variable voltage 82 or by any other suitable source. The test wires of each of the probes may be controlled by their respective heating circuits to selected temperatures.

At the upper portion of the inner conductor 58 is provided a sample tube 84 which is controlled by means of a sample valve 86. The sample tube allows a technician to withdraw a sample of the liquid under test if such is desired during or after the test procedure. The sample tube may also be employed for injection of a chemical constituent into the vessel if desired without necessitating disassembly or depressurization of the vessel.

Figure 3:
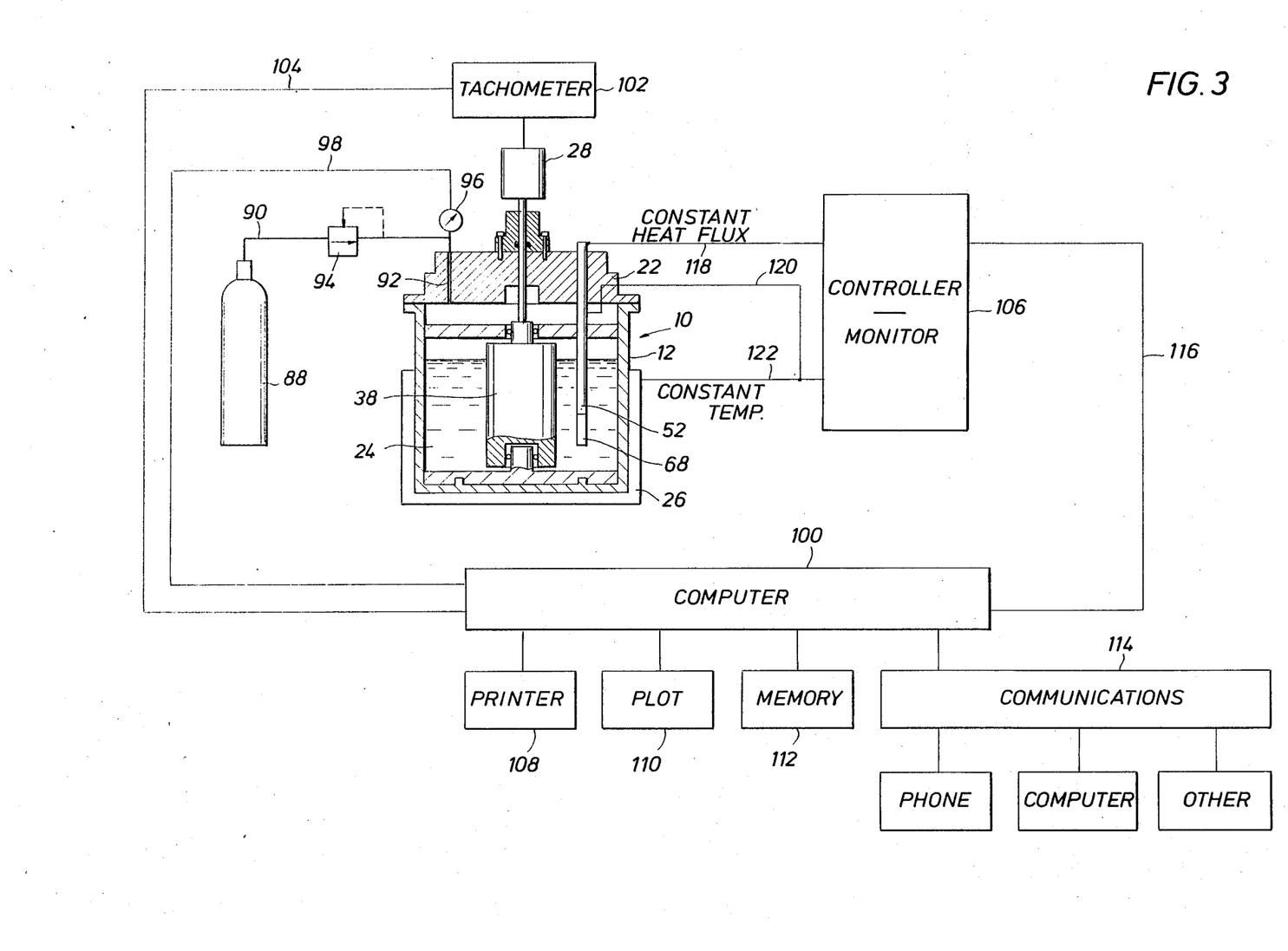
FIG. 3 is a diagrammatic illustration of apparatus, pneumatic circuitry and electronic circuitry for conducting anti-fouling according to the present invention.

With reference now to FIG. 3, the combination mechanical, pneumatic and electronic schematic illustrates the use of a high pressure gas for controlling of fouling conditions. A container 88 of high pressure gas which may take the form of air, oxygen, nitrogen, carbon dioxide, etc. is coupled via pneumatic line 90 with a gas supply passage supply 92 formed in the closure element 22. The pressure of the gas is controlled by a pressure regulator 94 to insure that the pressure maintained within the test chamber 24 is proper for the test being conducted. A pressure sensor 96 is coupled with conduit 90 and in addition to providing a visual indication of the pressure condition of the test chamber, also transmits via an electrical conductor 98 pressure signals to a computer 100. Additionally, the variable speed drive motor 28 is provided with a tachometer circuit 102 having its output coupled to the computer 100 by means of a suitable electrical circuit 104. The electrical current for each of the probes 52 is supplied from a Controller/Monitor power supply which provides a controllable constant heat flux, which in turn is controlled to provide either a constant heat flux supply or a constant temperature supply. All instructions for test control are provided by means of the computer 100 which compiles and directs the data to a printer 108, a plotter 110 and a computer memory 112 for storage. The computer is also provided with a communications port 114 for remote data collection such as by telephone, supplemental computer or other suitable source. The computer output is coupled via conductor 116 to the power supply of the Controller/Monitor. A plurality of conductors such as shown at 118 couple the Controller/Monitor power supply with the various probe 52 for heating the resistance wires 68. Conductors 120 and 122 provide the probes and the heating jacket 26 with controlled electrical energy for maintenance of a controlled temperature to the test unit.

The period for testing can be as short as one hour and can be extended for any period, however, it is usually conducted for a three hour period. The probe is first prepared by carefully measuring the weight and length of a small fouling test wire, then securing the test wire to the probe such as in the manner shown in FIG. 4. Test fluid is then introduced into the test chamber 24 and the probes are inserted into the vessel, sealed and brought up to desired temperature and pressure. The source 88 of compressed gas is used to charge the test chamber with the appropriate atmosphere and appropriate pressure for the test. During the process of the raising the fluid temperature, a small current is applied to the probe and the resulting voltage across the test wire, and therefore the resistance of the test wire, is measured. A calibration of test wire resistance versus temperature is obtained. A curve fitting program is used to determine the exact mathematical function which describes the, calibration. The mathematical function is then utilized to extrapolate to any desired probe test temperature. As a function of current the current is increased in order to achieve desired wire temperature. Two modes of continuing the tests are used: (1) For constant probe temperature, operational current is first applied for the apparatus to reach a selected starting temperature, and then the controller circuitry is set to maintain the starting temperature throughout the test. As fouling deposits accumulate, the probe current required to maintain constant temperature declines. A comparison of current versus time is used to develop a "current fouling curve" and is used as an in-situ fouling monitor. (2) For constant heat flux operation, a level of heat flux is applied sufficient to bring the probe to the desired temperature. This heat flux is maintained constant throughout the remainder of the test, during which time the probe surface temperature rises as a result of the insulating properties of the fouling deposit. The theory shows that the temperature increases directly proportional to the deposit amount. The temperature change versus time is called a "temperature fouling curve" and is used as an in-situ measure of fouling.

The fouling test apparatus of the present invention is utilized in laboratory conditions and produces a fouling deposit under controlled velocity, temperature and pressure conditions. The probe temperature is calibrated prior to each test and, therefore, close control is maintained over the fouling process. Fouling rates are evaluated by determining the amount of deposit which is found on the hot probe surface defined by the replaceable test wires. As deposits form, the heat transfers from the surface of the test probe wires is reduced and can be related to a fouling factor, which in turn, is proportional to the amount of deposit. That relationship is:

$$F = (1/u\ fouled) - (1/u\ clean) \qquad \text{Eq. (1)}$$

Where
F = Fouling Factor ($cm^2 \cdot °C/watts$)
U fouled = Heat transfer coefficient, fouled ($watts/cm^2 \cdot °C$)
U clean = Heat transfer coefficient, clean ($watts/cm^2 \cdot °C$)

The heat transfer coefficient is related to measurable parameters according to:

$$U = Q/A(T_s - T_o) \qquad \text{Eq. (2)}$$

Figure 5:
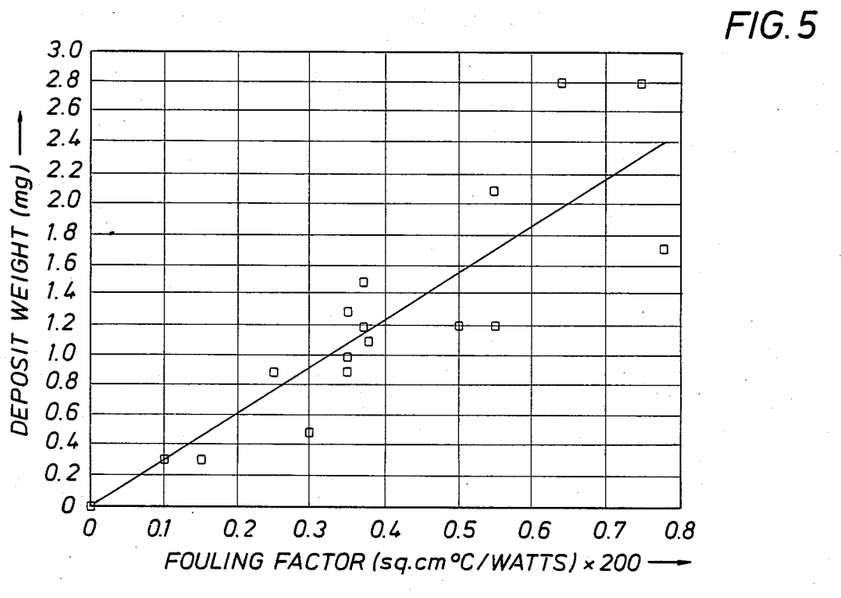
FIG. 5 is a graphical representation illustrating deposit weight vs. fouling factor for crude oil fouling tests.

Where
Q = Heat duty watts
A = Heat transfer area
$T_s$ = Metal temperature °C
$T_o$ = Oil temperature °C A number of tests were conducted according to the principles of the present invention. These tests resulted in a fouling curve which is the fouling factor defined by Equations 1 and 2 plotted vs. time. The test time was varied but typically a three hour test run time was adopted. Test pressure was maintained constant at 500 psi utilizing nitrogen introduced from a remote source. The probes were weighed before and after testing and a deposit weight was obtained along with each fouling curve. Deposit weight vs. fouling factor is shown by the graphical representation of FIG. 5. FIG. 5 is a plot of foulant deposit weight vs. fouling factor. The curve was generated by taking the final reading at the end of a number of fouling tests and comparing to the observed deposit weight. In order for this method to be of value, a direct relationship should exist between the fouling factor and the deposit weight. FIG. 5 indicates that this relationship is approximately linear. Photographs were made of each of the probe wires for visual indication of the physical character of the foulant accumulated on the respective probe wires.

Figure 6:
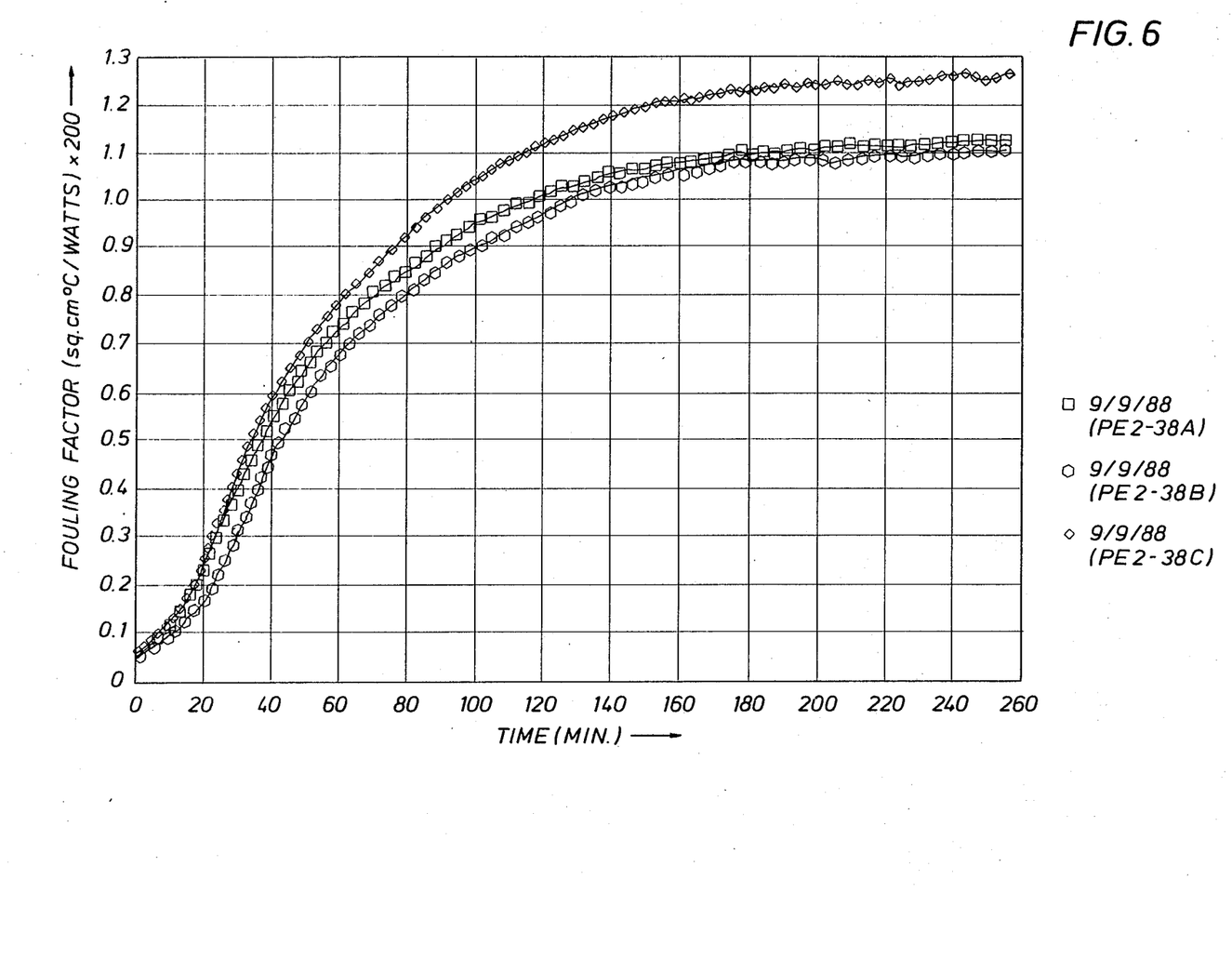
FIG. 6 is a graphical representation of the fouling factor vs. time which illustrates several fouling curves which together establish a baseline curve and demonstrates the test reproducability.
Figure 7:
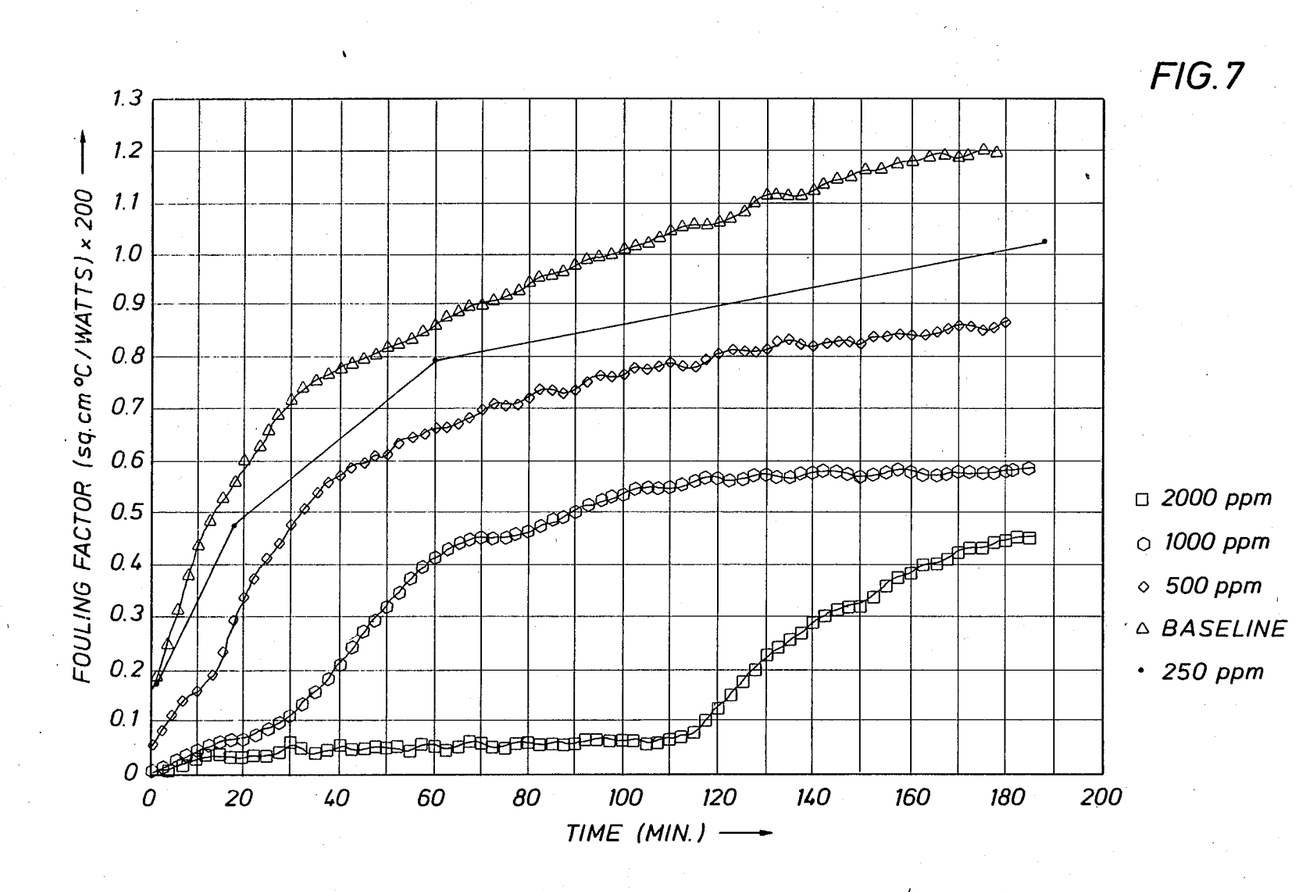
FIG. 7 is a graphical representation of fouling factor vs. time for a fluid sample and including a baseline curve and several curves illustrating the effect of a particular anti-fouling chemical concentration in the fluid being sampled.
Figure 8:
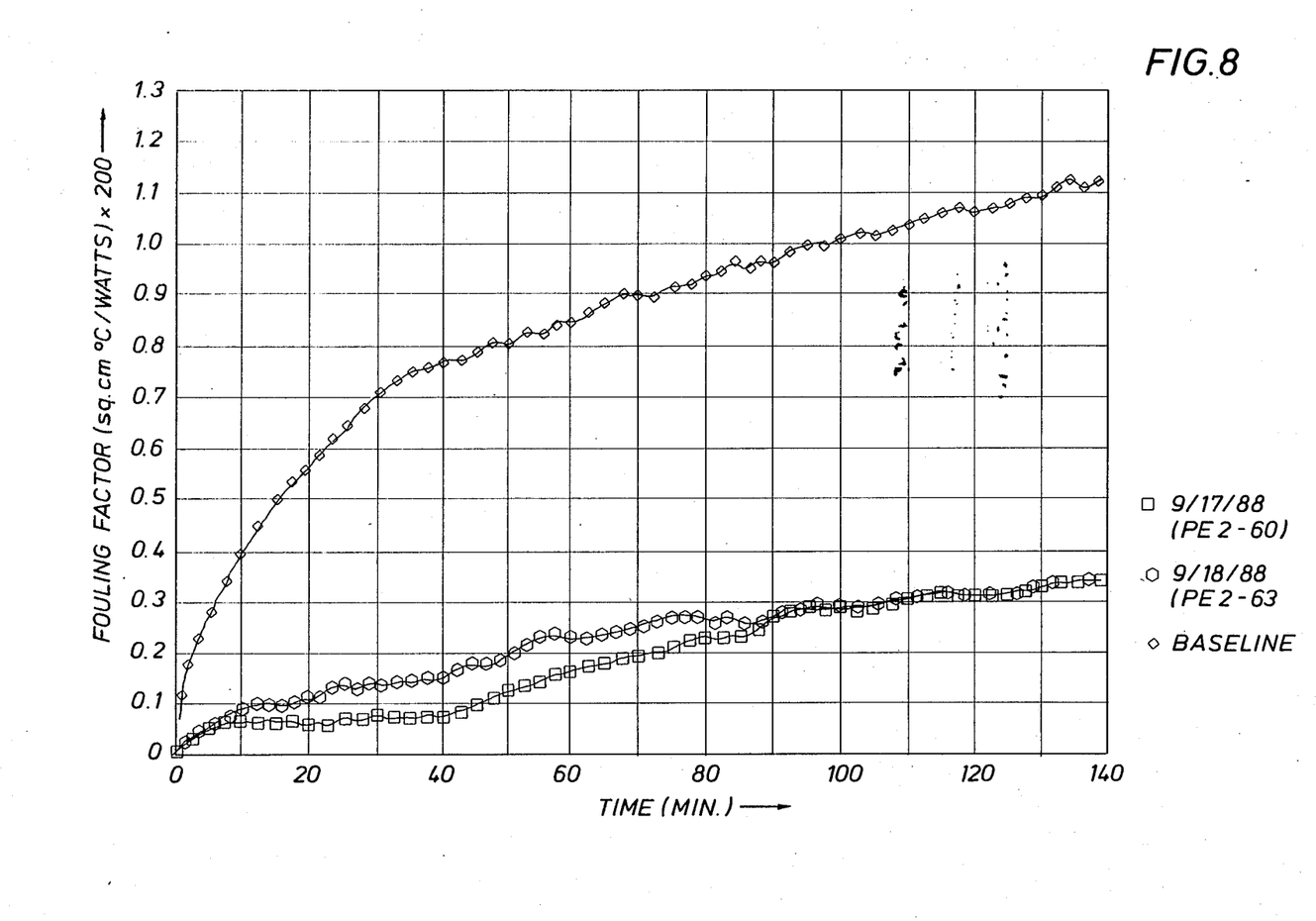
FIG. 8 is a graphical representation depicting fouling factor vs. time and showing test curves representing the baseline and multiple runs showing the reproducability effect of a selected concentration of anti-foulant being added in the fluid under test.

FIG. 6 is a graphical representation of baseline reproducibility where the fouling factor is compared vs. time. In FIG. 7 the graphical representation illustrates the effect of anti-foulant in the test sample. The graph of FIG. 8 compares the fouling factor against time and shows a baseline having the baseline reproduceability illustrated in FIG. 6. The lower portion of the plot, FIG. 8 illustrates chemical reproducability which in this particular test was obtained by the addition of 2000 ppm Mg OB. The reduction of fouling through the addition of chemical anti-foulant is obvious from FIG. 8.

Figure 9:
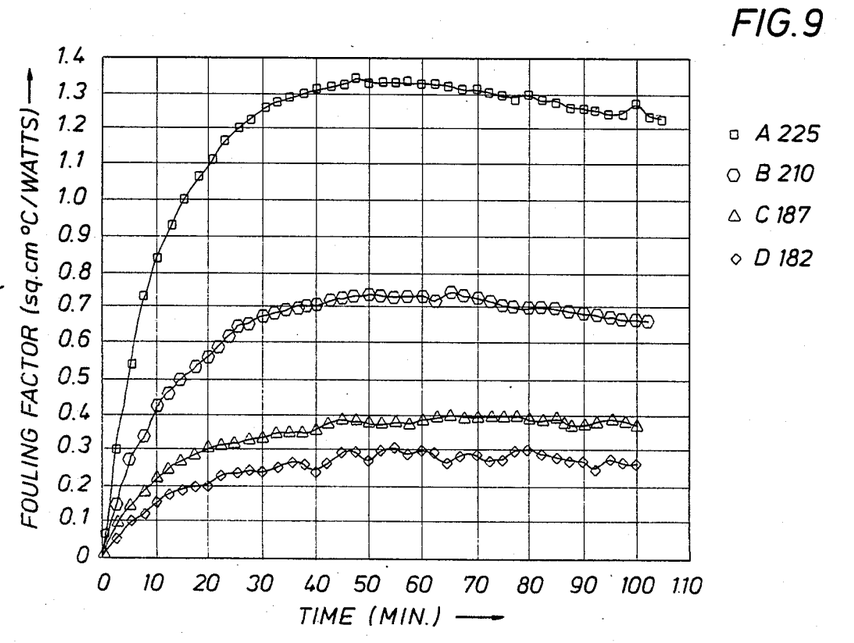
FIG. 9 is a graphical representation having several fouling factor vs. time curves representing the effect of metal temperature on fouling from a particular crude oil sample.

FIGS. 8 and 9 show the fouling rates and subsequent reduction of fouling deposits with anti-foulants for two different applications. The first application was a fractionation plant which processed produced crude oil. During this process hot tubular components became filed upon contact with the produced crude oil. The second application was a crude oil production field which was experiencing downhole fouling problems due to asphaltenes which came into contact with heated surfaces.

The reproducability of the baseline (no chemical) fouling conditions are illustrate in FIG. 6. Once a system is defined the overall baseline reproducability for this test is around plus or minus 5%. Also important is the reproducability of the chemical effect, and as shown in FIG. 6 the addition of a chemical anti-foulant yielded fouling test result that are considered quite good.

As shown in FIG. 7 the fouling factor vs. time plot illustrates a baseline curve and also illustrates the test curves which are yielded through addition of particular concentrations of anti-foulant chemical. Through laboratory tests, therefore, it can be determined the particular concentration of anti-foulant chemical that should be added for efficient operation of the fluid handling and controlling process.

According to the fouling factor vs. time plot of FIG. 9 the effects of metal temperature is quite significant in the control of the fouling factor. Under circumstances where metal temperature can be controlled the fouling factor may be sufficiently minimized without anti-foulant chemical additives simply by establishing the proper metal temperature. Under circumstances where metal temperature is not a controllable factor, the addition of anti-foulant composition is the only logical approach to minimizing fouling in fluid handling processes.

As a test procedure is initiated or determining the fouling aspects of a fluid sample, each of the wires to be utilized in the multiple probes of the apparatus are weighed. At the conclusion of the test each of the test probe wires is again weighed and compared with the beginning weight of the wires to thereby establish a net quantity of fouling per probe. This information is utilized in conjunction with other information from the test for determining the rate of fouling that is exhibited by the test samples and the particular parameters to which it is tested.

The multiple test probe unit of this invention employs an independently heated test wire for each probe. The wires may be operated at different temperatures during the test procedure, thereby enabling the development of multiple test results within a single test period thereby enhancing the commercial feasibility of the tests being conducted. The independently heated wires of each of the probes may be operated at constant power or at constant temperature depending upon the character of tests being conducted. When constant electrical power is employed the sensed temperature of the test probe continues to increase as fouling of the probe progresses. Due to the insulating properties of the fouling deposit. When the test probes are operated at constant temperature the electrical power required for heating the probe diminishes with the accumulation of fouling material also because of the insulating properties of the foulant. Depending upon the conditions involved the test probes may be operated at constant power or constant temperature to thereby enable laboratory personnel to quickly obtain test results through the acquisition of significant accumulation of data within a reasonably short period of time. Through utilization of test wire type probes, the fouling test apparatus is found to have a greater temperature range both at the high and low ends as compared with commercially available test apparatus. The electrical aspects of the fouling test apparatus of this invention are substantially different as compared with commercially available fouling test apparatus and procedures. In the case of the present invention the electric current is passed through the test wire for simultaneously heating the wire and measuring the temperature. The probe is utilized both as a detector and heater.

The test wires of the various probes have a low surface area to bulk oil volume ratio that is present within the testing chamber. The heating area of the wire is small and therefore the area of the wire exposed to the fluid under test has less of an impact on the quantity of foulant in the crude as compared to fouling test apparatus having much larger surface area in contact with the fluid. The testing apparatus of this invention is also capable of operating under turbulent flow wherein the fluid under test is highly stirred to increase the probability of particles coming together at the heated surface. When fouling tests are being conducted, different particles that are in suspended form in the solution under test come together at the heated surface of the test probe. When this occurs, the heat generated by the probe induces oxidation and/or polymerization to occur. Since oxidation and/or polymerization occurs at the heated surface, the particles that are developed by these processes readily adhere to the heated surface. In time these particles will accumulate and establish a layer which interferes with heat transfer such as in the case of heat exchangers and also reduces the cross-sectional dimension of the flow paths through which the fluid must flow. In the case of wells for production of petroleum products asphaltenes, paraffins, and other constituents of the fluid being produced, due to elevated temperatures at the production zone, have a tendency to become deposited on the inner surfaces of the tubing string utilized for production of the well. In many cases these deposits can be removed mechanically by well service apparatus but well production down time and well service expenses make it desirable to eliminate or minimize the build-up of these deposits. Various chemical additives may be effectively employed through utilization of specific chemicals and concentrations that are established through the outcome of tests conducted in accordance with this invention.

While the foregoing is directed to the preferred embodiment, the scope thereof is determined by the claims which follow.

What is claimed is:

1. Apparatus for conducting fouling deposit tests, comprising:
    (a) a pressure vessel including a sealed cylindrical test chamber for receiving a test fluid therein;
    (b) means for controlling the temperature of test fluid contained within said test chamber;
    (c) cylindrical rotary stirring means positioned in said pressure vessel concentrically with said cylindrical test chamber thereof;
    (d) means for rotating said stirring means;
    (e) a plurality of fouling test probes extending into said cylindrical test chamber, each of said fouling test probes having a removable electrically heated test wire located intermediate said cylindrical rotary stirring means and said cylindrical test chamber wall;
    (f) means sensing the accumulation of foulant on said test wires of said plurality of probes during the conduct of fouling test; and
    (g) wherein said plural test wires have finite lengths exposed to a common test fluid relative velocity resulting from operation of said rotary stirring means driven by said means for rotating.

2. The apparatus of claim 1, wherein:
said stirring means is powered by a variable speed electric motor.

3. The apparatus of claim 1, wherein:
    (a) upper and lower bearing supports are disposed within said test chamber; and
    (b) upper and lower bearings are axially located within said test chamber and support said cylindrical rotary stirring means for axial rotation within said test chamber.

4. The apparatus of claim 1, wherein:
    (a) said pressure vessel includes bottom and side walls and a removable closure; and
    (b) a drive shaft extends trough said removable closure and interconnects said means for rotating with said cylindrical rotary stirring means.

5. The apparatus of claim 4, wherein means for controlling the temperature of fluid contained in said pressure vessel comprises:
    (a) a heating mantle disposed about side and bottom wall surfaces of said pressure vessel; and
    (b) electrical circuitry including a power supply and a constant temperature control maintaining said heating mantle within a constant temperature range.

6. The apparatus of claim 1 wherein each of said plurality of fouling test probes comprises:
    (a) first and second conductor elements extending into said test chamber;
    (b) said fouling test wire having its ends coupled respectively with said first and second conductors; and (c) electrical heating circuit means including said first and second conductors operative to heat said fouling test wire to a predetermined temperature range.

7. The apparatus of claim 6 where said circuit means includes a constant temperature power supply and means for measuring the voltage across said fouling test wire for determining the resistance thereof.

8. The apparatus of claim 6 wherein said circuit means includes a constant current power supply and means for measuring the voltage of said test wire for determining the temperature of said fouling test wire.

9. The apparatus of claim 8, wherein:
(a) said first and second conductors connect to spaced test wire receptacles receiving end portions of said test wire; and
(b) locking means releasably secures said test wire with its end portions located within said receptacles.

10. The apparatus of claim 1 including:
a computer including a software program providing instructions for test control and said computer connects with data input and output circuits for (a) controlling pressure within said test chamber, (b) the rotation velocity of said means for rotating connected to said rotary stirring means, and (c) electrical current supplied to said plurality of test probe test.

11. The apparatus of claim 10 wherein said computer includes printer, plotter, memory and communication port circuits for compiling and directing data to and from said computer and for communicating computer data to remote locations for collection.

12. The apparatus of claim 1 wherein said test wires are parallel to an axis of rotation of said rotary stirring means.

13. The apparatus of claim 12 wherein said test wires are equal in length and located at the same radial distance from said rotary stirring means axis.

14. The apparatus of claim 12 wherein said test wires are equal in length and exposed to test fluid relative velocity resulting from sustained rotation of said rotary stirring means.

15. The apparatus of claim 12 wherein said test wires are mounted by said test probes outboard thereof relative to the axis of rotation of said rotary stirring means.

* * * * *